United States Patent [19]

Shah et al.

[11] Patent Number: 5,318,781

[45] Date of Patent: * Jun. 7, 1994

[54] ABSORPTION ENHANCEMENT OF ANTIBIOTICS

[75] Inventors: Navnit Shah, Clifton; Joel Unowsky, Livingston, both of N.J.

[73] Assignee: Hoffmann-La Roche Inc., Nutley, N.J.

[*] Notice: The portion of the term of this patent subsequent to Mar. 2, 2010 has been disclaimed.

[21] Appl. No.: 43,419

[22] Filed: Apr. 6, 1993

[51] Int. Cl.$^5$ .................. A61K 9/66; A61K 31/545
[52] U.S. Cl. ........................... 424/455; 514/202; 514/206; 514/786; 514/946
[58] Field of Search ............... 424/455; 514/202, 206, 514/786, 946

[56] References Cited

U.S. PATENT DOCUMENTS

| | | | |
|---|---|---|---|
| 3,516,997 | 6/1970 | Hirakatu et al. | 260/243 |
| 3,641,021 | 2/1972 | Ryan | 260/243 |
| 4,152,432 | 5/1979 | Heynes et al. | 424/246 |
| 4,224,371 | 9/1980 | Amiard et al. | 424/246 |
| 4,327,210 | 4/1982 | Montavon et al. | 544/27 |
| 4,406,896 | 9/1983 | Higuchi et al. | 424/232 |
| 4,476,123 | 10/1984 | Labeeuw et al. | 424/246 |
| 4,525,339 | 6/1985 | Behl et al. | 424/16 |
| 4,604,387 | 8/1986 | Labeeuw et al. | 514/206 |
| 4,722,941 | 2/1988 | Eckert et al. | 514/784 |
| 4,732,753 | 3/1988 | Fuller | 424/85 |
| 4,808,711 | 2/1989 | Shimizo et al. | 540/227 |
| 4,946,837 | 8/1990 | Miyake et al. | 514/206 |
| 5,190,748 | 3/1993 | Bachynsky et al. | 424/78.08 |

FOREIGN PATENT DOCUMENTS 0091502 10/1983 European Pat. Off. .
0126348 11/1984 European Pat. Off. .

OTHER PUBLICATIONS

Beskid et al., *Medline Abstracts*, No. 88271025, 1988.
Bachynsky et al., *Chemical Abstracts*, vol. 114(8), No. 69060j, 1990.
Miyamoto et al., J. Pharm. Sci., 72 651–654 (1983).
Derwent Abstract 82-96018E/45 of Japanese Patent Publication No. 57158719 (1982).

*Primary Examiner*—Frederick E. Waddell
*Assistant Examiner*—William R. A. Jarvis
*Attorney, Agent, or Firm*—George M. Gould; George W. Johnston; John P. Parise

[57] ABSTRACT

The oral absorption of antibiotics given of administration is significantly enhanced by use of the antibiotic in conjunction with a two-component absorption enhancing system made up of Laureth-12 together with a second component salts of capric acid and caprylic acids. The antibiotic containing two component enhancer system includes Miglyol-812 for optimum absorption.

16 Claims, No Drawings

ABSORPTION ENHANCEMENT OF ANTIBIOTICS

BACKGROUND OF THE INVENTION

1. Field of the Invention

The Invention concerns improved oral formulations for cephalosporin antibiotics.

2. Description of Prior Art

Since the first penicillin compounds were used successfully to fight pathogenic organisms such as bacteria, several generations of new anti-infective agents have been developed. Some of these agents, such as ceftriaxone, streptomycin, gentamicin and cefazolin, are normally poorly absorbed through mucosal tissue into the bloodstream and are, therefore, of limited or no practical value when administered via any route other than parenteral to fight systemic bacterial infections. Administration of these difficult-to-absorb drugs is sometimes accomplished by infusion, but more typically by intravenous or intramuscular injections.

Some injectable antibiotics, such as ceftriaxone, can be administered once a day and are therefore more convenient to use. However, for the most part, injectable antibacterial drugs must be given more frequently than once daily to achieve greatest effectiveness, and such treatments often require the services of a doctor, nurse or trained technician on a continual basis. The experience of frequent injections can also be distressful or unnerving for some patients.

Efforts have been made to find materials which promote the absorption of antibiotics and other pharmaceuticals that normally are poorly absorbed through mucosal tissue, the objective being to enable the formulation of non-injectable dosage forms such as capsules, tablets, pills, suppositories, and so forth with such pharmaceuticals. Some substances, such as ionic surfactants, sodium lauryl sulfate and chelating agents (e.g., EDTA) are known to be rather harmful to the mucosal membrane, although they have been reported to enhance the intestinal absorption of large molecules. On the other hand, as described in the patent literature, the enhanced rectal absorption of antibiotics is obtained by the use of promoters such as hydroxy aromatic acid salts (e.g., sodium salicylate and sodium homovanillate) U.S. Pat. No. 4,406,896 (Higuchi et al.); cholic acid or its salt together with a fatty acid glyceride (e.g., Witepsol ® manufactured by Dynamid Nobel) and a polyethylene alkyl ether, Japan patent publication No. 57158-719; cholic acid or its salt together with a fatty acid glyceride, Japan patent publication No. 5062-007; a fatty acid glyceride (e.g., Witepsol ®) together with a polyoxyethylene glycol (PEG)-fatty acid ester, U.S. Pat. No. 4,732,753 (Füller); and a bile acid in combination with a polyoxyethylene-fatty acid ester and a glycerol-fatty acid ester, U.S. Pat. No. 4,156,719 (Sezaki).

The absorption promotion of orally delivered antibiotics with the use of a cholic acid salt or taurocholic acid salt is described by Miyamoto et al., in J. Pharm. Sci. 72, 651-654 (1983).

U.S. Pat. No. 4,525,339 (Behl et al.) discloses active oral dosage forms of beta-lactam antibiotics using $C_2$–$C_{12}$ fatty acid mono-, di- or triglycerides as the absorption enhancer.

The permucosal absorption of various therapeutics, including antibiotics, is reported to be enhanced by the use of fatty acids and saturated or unsaturated fatty acid glycerides, in Swiss patent publication No. 634,749 corresponding to U.S. Pat. No. 4,722,941.

U.S. Pat. No. 5,190,748, assigned to Hoffmann-La Roche Inc., discloses oral dosage forms of cephalosporin antibiotics using polyethylene glycol lauryl ether (e.g., Laureth ®-12), salts of caprylic acid/capric acid (e.g., sodium caprylate), and a carrier such as Witepsol ® H15. For completeness, the disclosure in such patent is incorporated herein by reference.

European Patent Application No. 126,348 (Mori) describes compositions for rectal administration containing a polyoxyethylene alkyl ether and a $C_{8-10}$ fatty acid salt, an oleaginous base, as well as a cephalosporin antibiotic. The fatty acid may be caprylic acid and its salts including alkaline metal salts. The polyoxyetheylene alkyl ether includes polyoxyethylene (21) lauryl ether (i.e., Laureth-21). The base includes fatty acid glycerol esters (e.g., Witepsol ®).

In European Patent Application No. 91,502, Yata describes rectal formulations for cephalosporins which formulations include a cephalosporin (e.g., ceftriaxone), an olegnous base (e.g., Miglyol ® manufactured by Hulls America, or Witepsol ®), an amino acid, and an ether-type nonionic surfactant (e.g., polyoxyethlene alkyl ethers).

While certain of the above formulation may enhance delivery, applicants surprisingly have discovered a unique formulation which optimizes the oral delivery of cephalosporins. Applicants unique combination of known components gives rise to superior absorption results.

SUMMARY OF THE INVENTION

Drug levels sufficient to treat or prevent bacterial infections in a host can be achieved by orally administering to the host a prophylactic or therapeutic effective amount of a pharmaceutical suspension composition comprising (a) a water soluble cephalosporin; (b) an absorption enhancing amount of a two-component absorption enhancing system made up of (1) polyethylene glycol-12 (PEG) lauryl ether (i.e., Laureth-12), and (2) a pharmaceutically acceptable salt of caprylic or capric acid; and (c) a $C_8$–$C_{10}$ triglyceride carrier (i.e., Miglyol ®-812). The composition can be placed in a capsule which is coated with a pharmaceutically acceptable enteric coating.

It is the unique combination of the two-component absorption enhancement system and the carrier, in an enteric coated vehicle which gives rise to the superior results.

The above composition increases the extent of absorption of antibacterial compounds through mucosal tissue and into the bloodstream. This invention thus promotes the absorption and, concomitantly, the bioavailability of antibacterial compounds. The invention also promotes the greater absorption and bioavailability of antibacterial compounds which are otherwise only moderately absorbed through mucosal tissue, thus enhancing the effectiveness of such therapeutic compounds.

This invention also encompasses the administration of the aforementioned pharmaceutical composition in unit dosage form suitable for oral administration.

DETAILED DESCRIPTION OF THE INVENTION

The present invention describes a method for treating a bacterial infection in a host comprising orally administering to the host a therapeutic effective amount of a pharmaceutical suspension composition comprising:
a) a water soluble cephalosporin;
b) an absorption enhancing amount of an absorption enhancing system including:

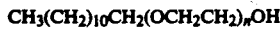 (1)

wherein n has an average value of 12; and
2) a pharmaceutically acceptable salt of at least one of caprylic or capric acid, wherein the weight ratio of component (b)(1) to component (b)(2) is from about 1:6 to about 6:1, preferably about 1:1, and most preferably about 6:5.
c) a compound of the formula:

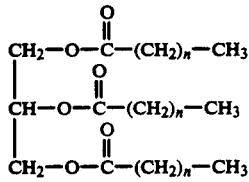

wherein n is 6 or 8.

The composition is placed in a suitable vehicle such as a capsule and the vehicle is coated with a pharmaceutically acceptable enteric coating.

The invention also includes a unit dose capsule pharmaceutical composition comprising:
a) a therapeutic effective amount of a water soluble cephalosporin; and
b) an absorption enhancing amount of an absorption enhancing system including:
(1) a compound of the formula:

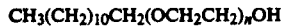

wherein n has an average value of 12; and
(2) a pharmaceutically acceptable salt of at least one of caprylic acid and capric acid, wherein the weight ratio of component (b)(1) to component (b)(2) is from about 1:6 to about 6:1, more preferably about 1:1, and most preferably about 6:5; and
c) a compound of the formula:

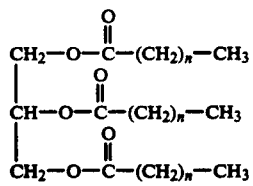

wherein n is 6 or 8,
said unit dose being placed in a vehicle such as capsule which is coated with a pharmaceutically acceptable enteric coating.

The term "host" includes mammals, preferably humans.

The terms "antibacterial" and "antibiotic" are used interchangeably throughout this disclosure to refer to bactericidal or bacteriostatic compounds which have been metabolically derived from a microorganism, synthetically prepared by chemical means, or prepared by a combination of microbial and chemical procedures (semi-synthetic).

Antibacterial compounds include beta-lactam antibiotics, particularly compounds having a beta-lactam ring for its central structure as follows:

which can be substituted at various positions on the ring and/or fused with other ring systems which themselves can be substituted or unsubstituted. Exemplary of such beta-lactam antibiotics are penicillins, cephalosporins, penems, carbapenems and monocyclic beta-lactams.

In this disclosure, a "cephalosporin" means those antibacterial compounds which have as their central structure:

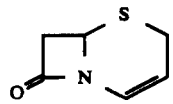

which can substituted at various positions on the ring, which in turn can be substituted or unsubstituted.

Especially preferred water soluble cephalosporins (component (a)) and their pharmaceutically acceptable salts, esters and hydrates include ceftriaxone, a cephalosporin described in U.S. Pat. No. 4,327,210 (Montavon et al.); and cefotaxime, described in U.S. Pat. Nos. 4,152,432 and 4,224,371. Further cephalosporins include cefamandole, a cephalosporin described in U.S. Pat. No. 3,641,021; cefazolin, a cephalosporin described in U.S. Pat. No. 3,516,997, the disclosures of all of these patents identified in this paragraph are incorporated herein by reference. Further cephalosporins included are cefoxitin, cefmetazole, cefotetan, cefuroxime, ceforamide, cefoperazone, ceftizoxime, cefotaxime, cefmenoxime and ceftazidime. See also the water soluble cephalosporins in U.S. Pat. Nos. 4,476,123; 4,604,387; 4,808,711; and 4,946,837.

The most preferred water soluble cephalosporin is ceftriaxone which has the formula:

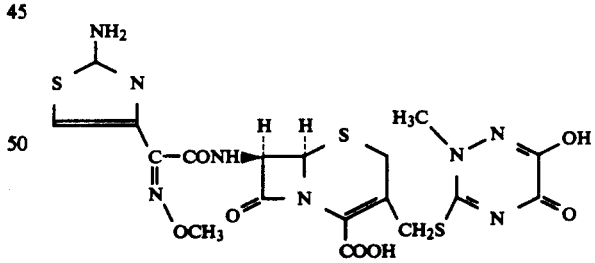

Laureth-12, the first component of the enhancing system (component (b)(1)), is the product of an etherification reaction between laurel alkanol and polyoxyethylene glycol. Laureth-12 has the formula:

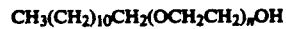

wherein n has an average value of 12.

Laureth-12, having a CTFA designation of PEG (12) Lauryl ether, is commercially available and also known as MACOL ® LA-12, manufactured by Mazer Chemicals Company, Gurnee, Ill.; Alkasurf ® LAN-12, having a CTFA designation of PEG (12) Lauryl ether, is commercially available and also known as MACOL® LA-12, manufactured by Mazer Chemicals Company, Gurnee, Ill.; Alkasurf® LAN-12, manufactured by Alkaril; Carsonon® L-12, manufactured by Lonza; and Ethosperse® LA-12, manufactured by Glyco.

The polyoxyethylene glycol in Laureth-12 is, typically, a medium to high molecular weight material which preferably has a number average molecular weight of 600.

The second component of the enhancing system (component (b)(2)) is one or more of the salts of caprylic and capric acid.

Caprylic acid has the formula:

$CH_3(CH_2)_6COOH$.

Capric acid has the formula:

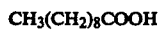
$CH_3(CH_2)_8COOH$

In accordance with the invention, the pharmaceutically acceptable salts of either or both of capric acid and caprylic acid, or mixtures thereof can be used and are contemplated by the invention. The salts can be prepared in a conventional manner and using known techniques by reacting the acid with a base having a nontoxic, pharmacologically and pharmaceutically acceptable cation. In general, any base which will form a salt with the carboxylic acid and the pharmacological properties of which will not cause an adverse physiological effect when ingested by or otherwise administered to a warm-blooded animal is suitable. Such bases thus include, for example, alkali metal and alkaline earth metal hydroxides or carbonates, such as sodium hydroxide, potassium hydroxide, calcium hydroxide, potassium carbonate, and the like. Particularly preferred for this invention are sodium salts, chiefly because of their ready availability, and potassium salts. Sodium caprylate is most preferred.

Component (c) of the inventive formulation is known as Miglyol-812, which is a $C_8$–$C_{10}$ triglyceride of the formula:

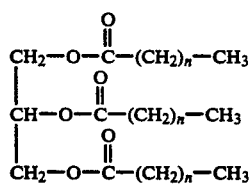

wherein n is 6 or 8. Miglyol-812 is manufactured by Hulls America, as well as Drew Chemicals under the trademark Neobee®.

Suitable enteric coating materials for this invention include any conventional enteric coating such as but not limited to the following:
cellulose acetate phthalate ("CAP")
cellulose acetate trimellitate
hydroxypropyl methylcellulose phthalate ("HPMCP")
hydroxypropyl methylcellulose phthalate succinate
polyvinyl acetate phthalate ("PVAP")
methacrylic acid
methacrylic acid esters Preferably, PVAP and/or HPMCP, particularly PVAP, are utilized as the enteric coating. PVAP is known under the trademark Opadry® Enteric Orange, manufactured by Colorcon, Inc. The enteric coating materials may be applied to the vehicle (e.g., capsule) with or without conventional plasticizers, such as acetylated mono glycerides or diethylphthalate, using methods known to those skilled in the art.

Usage of enteric coating materials serves to protect the antibacterial compound from the gastric fluid and/or to achieve optimum delivery of the antibacterial compound together with the absorption enhancing system to the intestine. The enteric coating material is selected to be resistant to the gastric fluid but able to dissolve in the intestinal fluid to cause release of the drug. The effectiveness of particular enteric coating materials can be measured using known USP procedures.

The relative proportions of the components in the inventive composition can be varied to achieve optimum absorption depending on the cephalosporin selected. For the water soluble caphalosporins and in particular ceftriaxone sodium, the composition by weight can range as follows:

a) about 10% to about 50% ceftriaxone sodium, preferably about 30% to about 50%, most preferably about 40%;

b)
1) about 5% to 30% Laureth-12, preferably about 15% to about 25%, and most preferably about 17–20%;
2) about 5% to about 30% of the salt of caprylic/capric acid, preferably about 10 to about 25%, and most preferably about 15%;

c) about 15% to about 50% of Miglyol-812, preferably 20% to about 40%, and most preferably about 30%;

d) about 2% to about 15% enteric coating preferably about 4% to about 10%, and most preferably about 7%;

In a preferred embodiment, the salt of caprylic/capric acid is sodium caprylate, which is present in the above ceftriaxone composition in the above weight percentages. The enteric coating, preferably polyvinylacetate phthalate ("PVAP"), is present in the above percentages.

The inventive compositions are in the form of an enteric coated liquid suspension dosage form. The formulation can be filled into a hard or soft-shell capsule or their equivalent and the capsule is coated with the enteric coating in accordance with conventional techniques.

The term "unit dose" is used herein in the conventional sense to mean a single application or administration of the drug to the subject being treated in an amount as stated below. It should be understood that the amount can be given in one unit dose or capsule, or alternatively, in multiples of two or more of such dose units with the total adding up to the stated amount of drug for a given time period.

In general, for the oral unit dosage form compositions of this invention, it is preferred to employ from about 50 to about 1000 milligrams (mg), and more preferably from about 100 to about 500 mg of the absorption enhancing system (component b (1) and (2)) for each unit dose of the composition. These compositions will usually contain the cephalosporin in amounts from about 10 to about 500 mg, and more preferably from about 200 to about 350 mg, per unit dose. The actual amount will vary depending upon the cephalosporin selected.

For sodium ceftriaxone, the oral unit dosage form can range as follows:

a) about 50 mg to about 500 mg sodium ceftriaxone, preferably 100 mg to about 350 mg, more preferably about 200 mg to about 300 mg, and most preferably about 250–300 mg.;

b)
1) about 25 mg to about 300 mg of Laureth-12, preferably about 50 mg to about 200 mg, and most preferably about 120 mg;
2) about 25 mg to about 300 mg of the salt of caprylic/capric acid, preferably about 50 mg to about 200 mg, and most preferably about 100 mg;

c) about 100 mg to about 400 mg of the Miglyol-812, preferably about 150 mg to about 300 mg, and most preferably about 250 mg.

d) about 25 mg to about 150 mg of the enteric coating, preferably about 50 mg to about 100 mg, and most preferably about 70 mg.

In a preferred embodiment, the salt of the caprylic/capric acid is sodium caprylate, which is present in the above weight amounts. The enteric coating, preferably polyvinyl actate phthlate ("PVAP"), also is present in the above amounts.

Experimental Examples

To evaluate the mucosal tissue absorption of cephalosporins administered in accordance with this invention, in vivo tests were conducted on the inventive compositions as well as compositions known from the prior art. In particular, the inventive compositions which contain Miglyol-812 were compared against formulations containing Witepsol-H15 rather than Miglyol-812. The procedures and results are described in Examples 1 through 3.

EXAMPLE 1

In Vivo (Rats)—Enteral

Adult Sprague-Dawley female rats (Charles River Breeding Laboratories, Kingston, N.Y.), weighing about 250 grams each, were fasted overnight and anesthetized with metofane. With each rat, an incision was made on the ventral surface to expose the intestine. Administration of an antibiotic at a give dose was carried out using a solution dosage form. The solutions were prepared by dissolving 5 mg of antibiotic in water with or without absorption enhancer and diluting to the desired concentration.

Each solution of antibiotic in water was administered enterally by injecting with a syringe into the duodenum below the pyloric valve. For purposes of comparison with the enteral administration, the solution alternatively was administered intravenously ("I.V.") by injecting with a syringe into a tail vein.

Plasma Levels of Antibiotic in Rats

The concentration of antibiotic in rat plasma was determined at various time intervals after intravenous or enteral administration. Blood samples were collected from the tail of each test animal prior to administration of the antibiotic and at 5, 10, 20, 40, 60, 120, 240 and 360 minutes after administration, then centrifuged at 3200 rpm for 5 to 10 minutes, after which the plasma was withdrawn and frozen until assayed.

Bioassay of Plasma Samples in Rats

Antibiotic levels in plasma (Cmax) were assayed on nunc plates employing the appropriate agar seeded with bacteria, as listed below.

| Antibiotic | Assay Organism | Bioassay of Plasma Range of Standard Curves (mcg/ml) | Bioassay Media | Volume (mcl) |
|---|---|---|---|---|
| CEFTRIAXONE | E. coli 1346 | 8–0.25 or 16–0.5 | AA#1 | 20 |
| CEFOTAXIME | E. coli 1346 | 4–0.125 | AA#1 | 20 |

AA#1 = Antibiotic agar #1 manufactured by Difco, Inc., (Detroit, Michigan).
mcg/ml = micrograms per milliliter
mcl = microliters The plates were incubated overnight at 37° C. and the zones of inhibition were read to the nearest 0.1 mm. Calculations of $C_{max}$ and $C_{max}$ Ranges were made using an autoassay machine (Giles Scientific, Inc., New York). For reference, see J. V. Bennett et al., Applied Microbiology 14, 170–177 (1966).

In this rat enteral experiment, inventive compositions containing Miglyol-812 as a component were compared with compositions containing Witepsol-H15 as a component. Two cephalosporins were utilized. The formulations are shown in Tables 1A (ceftriaxone) and 1B (ceftaxime) below:

TABLE 1A

| Ingredients | Ceftriaxone Control | Formula 1 | Formula 2 |
|---|---|---|---|
| CEFTRIAXONE | 6.0 mg | 6.0 mg | 6.0 mg |
| WATER | 0.5 ml | — | — |
| SODIUM CAPRYLATE | — | 2.5 mg | 2.5 mg |
| LAURETH-12 | — | 3.0 mg | 3.0 mg |
| MIGLYOL-812 | — | 8.5 mg | — |
| WITEPSOL-H15 | — | — | 8.5 mg |

TABLE 1B

| Ingredients | Cefotaxime Control | Formula 1 | Formula 2 |
|---|---|---|---|
| CEFOTAXIME | 6.0 mg | 6.0 mg | 6.0 mg |
| WATER | 0.5 ml | — | — |
| SODIUM CAPRYLATE | — | 2.5 mg | 2.5 mg |
| LAURETH-12 | — | 3.0 mg | 3.0 mg |
| MIGLYOL-812 | — | 8.5 mg | — |
| WITEPSOL-H15 | — | — | 8.5 mg |

The results of the rat enteral experiment for Cmax and Cmax Range are shown on Table 1C and 1D, respectfully, for the compositions of Tables 1A and 1B.

TABLE 1C

Enteral Absorption in Rats
Dose = 20 mg/kg of rat delivered in 0.5 ML
Cmax (mcg/ml)(average)

| Antibiotic | Control (Water) | Formula 1 | Formula 2 |
|---|---|---|---|
| CEFTRIAXONE | 2.4 ± 1.9 | 83 ± 16 | 8.3 ± 4.5 |
| CEFOTAXIME | 2.9 ± 1.8 | 17.3 ± 5.3 | 6.7 ± 5.6 |

TABLE 1D

Enteral Absorption in Rats
Dose = 20 mg/kg of rat delivered in 0.5 ML
Cmax Range (mcg/ml)

| Antibiotic | Control (Water) | Formula 1 | Formula 2 |
|---|---|---|---|
| CEFTRIAXONE | .8–6 | 65–101.9 | 5–14.5 |
| CEFOTAXIME | .4–.7 | 13.6–26.5 | 3.3–15 |

The data of Tables 1C and 1D indicate that Formulas 1 and 2, particularly those with ceftriaxone, were superior compared to control in terms of Cmax values and Cmax Range. Moreover, inventive Formula I was superior to prior art Formula 2 in terms of Cmax values and Cmax Ranges for rats.

EXAMPLE 2

In Vivo (Baboons)—Oral

Adult baboons, ranging in weight from 12 to 30 kilograms, were used in this study. The baboons were fasted overnight, then sedated with ketamine hydrochloride by intramuscular injection prior to administration of the antibiotic. Each baboon received one or two hard shell gelatin capsules, enteric coated with Opadry Enteric polyvinyl acetate phthalate (approximately 8% of total capsule weight), through a gastric tube. The composition of each capsule is shown in Tables 2A (one capsule) and 2B (two capsules), below, in which ceftriaxone was utilized as the antibiotic.

One-milliliter blood samples were taken from the femoral region of each baboon using a heparinized 3-ml syringe. Samples were taken prior to ceftriaxone administration and at 0, 60, 240, 360, 480, 600 and 720 minutes following ceftriaxone administration. The samples were centrifuged at 12,000 rpm for one minute and the plasma was separated and bioassayed for antibiotic content after deproteinization with acetonitrile, using the same procedure with respect to the baboons as described previously for the Bioassay of Plasma Samples in Rats (see Experiment 1).

Plasma level as a function of time was ploted for each baboon. Through the use of a computer system, the area under the curve ("AUC") was determined for oral and I.V. route of administration for each baboon. The bioavailability then was computed as follows:

$$\% \text{ Bioavailability} = \frac{\text{AUC (oral)} \times \text{I.V. Dose}}{\text{AUC I.V.} \times \text{oral dose}} \times 100$$

The results also are shown in Tables 2A (one capsule) and 2B (two capsules).

TABLE 2A

ORAL ABSORPTION OF CEFTRIAXONE IN BABOONS
(1 CAPSULE)
FORMULATIONS

| INGREDIENTS (per capsule)[1] | FORMULA 1 (mg) | FORMULA 2 (mg) | CONTROL (mg) |
|---|---|---|---|
| CEFTRIAXONE, SODIUM [2] | 300 | 240 | 240 |
| LAURETH-12 | 120 | 120 | — |
| SODIUM CAPRYLATE | 100 | 100 | — |
| MIGLYOL-812 | 250 | — | — |
| WITEPSOL-H15 | — | 230 | 450 |
| TOTAL WEIGHT OF CAPSULE | 770 | 690 | 690 |
| CEFTRIAXONE DOSE/BABOON[2] | 250 | 200 | 200 |
| RESULTS | | | |
| % BIOAVAILABILITY (average) | 6.9 ± 5.7 | 8.3 ± 5.5 | 0 |
| Cmax (mcg/ml)(average) | 5.8 ± 5.1 | 5.5 ± 2.8 | 0 |
| Cmax Range (mcg/ml) | 0–11.4 | 0–8.5 | 0 |

[1] enteric coated with Opadry Enteric Orange, approximately 8% of total capsule weight excluding the capsule itself).
[2] 300 mg and 240 mg of ceftriaxone sodium are equivalent to 250 mg and 200 mg ceftriaxone, respectively.

TABLE 2B

ORAL ABSORPTION OF CEFTRIAXONE IN BABOONS
(2 CAPSULE)
FORMULATIONS

| INGREDIENTS (per capsule)[1] | FORMULA 1 (mg) | FORMULA 2 (mg) | CONTROL (mg) |
|---|---|---|---|
| CEFTRIAXONE, SODIUM [2] | 300 | 240 | 240 |
| LAURETH-12 | 120 | 120 | — |
| SODIUM CAPRYLATE | 100 | 100 | — |
| MIGLYOL-812 | 250 | — | — |
| WITEPSOL-H15 | — | 230 | 450 |
| TOTAL WEIGHT OF CAPSULE | 770 | 690 | 690 |
| CEFTRIAXONE DOSE/BABOON[2] | 500 | 400 | 400 |
| RESULTS | | | |
| % BIOAVAILABILITY (average) | 16.3 ± 7.1 | 15.9 ± 8.2 | 1.4 ± 3.4 |
| Cmax (mcg/ml)(average) | 21.1 ± 8.5 | 14.5 ± 6.0 | 1.3 ± 3.1 |
| Cmax Range (mcg/ml) | 6.3–30 | 5.9–27.5 | 0–7.5 |

[1] enteric coated with Opadry Enteric Orange, approximately 8% of total capsule weight).
[2] 300 mg and 240 mg of ceftriaxone sodium are equivalent to 250 mg and 200 mg ceftriaxone, respectively.

The results indicate that Formula 1 (Miglyol-812) and Formula 2 (Witepsol H15) demonstrated better bioavailability and Cmax values than the control formulation

EXAMPLE 3

Oral Bioavailability in Humans—Oral

After overnight fasting, six human subjects weighing about 60–80 kgs each were administered one or two capsules of the test formulations. The blood samples for the subject's plasma combination were withdrawn at 0, 0.5, 1.0, 1.5, 2.0, 2.5, 3.0, 3.5, 4.0, 5.0, 6.0, 7.0, 8.0, 10.0, 12.0, 14.0, 16.0 and 24.0 hour time intervals. The data was plotted as plasma concentration for each subject as a function of time. Area under the curve ("AUC") was calculated as described in Example 2.

The plasma concentration (Cmax) for each time interval was determined by a reverse phase chromatographic method (HPLC). All chromatographic procedures were performed at ambient temperature. The column was a Hamilton PRP-1 column. The conditions used during analyses were a flow rate of 1.0 ml/min, an injection volume of 100 µl, and a detector wavelength of 270 nm. The isocratic mobile phase consisted of two phases. Mobile phase A consisted of 0.01M tetradecyltrimethylammonium bromide+0.05M potassium phosphate dibasic diluted in 1 liter of HPLC grade water, pH adjusted to 7.0 with phosphoric acid, 85 wt. % solution in water. Mobile phase B consisted of 0.01M tetradecyltrimethylammonium bromide+0.05M potassium phosphate dibasic diluted to 1 liter in 50% acetonitrile in water, pH adjusted to 7.0 with phosphoric acid, 85 wt. % solution in water. Mobile phase A was mixed with mobile phase B by the pumpion action system to achieve a final concentration by volume of 30% acetonitrile (40% A, 60% B). The lower limit of HPLC sensitivity was equal to 1.0 µg/ml.

The test formulations and results are shown in Tables 3A (one capsule) and 3B (two capsules).

TABLE 3A (One capsule)
ORAL ABSORPTION OF CEFTRIAXONE IN HUMANS
FORMULATIONS

| INGREDIENTS (per capsule)[1] | FORMULA 1 (mg) | FORMULA 2 (mg) |
|---|---|---|
| CEFTRIAXONE, SODIUM[2] | 300 | 240 |
| LAURETH-12 | 120 | 120 |
| SODIUM CAPRYLATE | 100 | 100 |
| MIGLYOL-812 | 250 | — |
| WITEPSOL-H15 | — | 230 |
| TOTAL | 770 | 690 |
| CEFTRIAXONE DOSE[2] | 250 | 200 |
| RESULTS | | |
| Cmax mcg/ml (average) | 8.3 ± 4.7 | 1.6 ± 0.7 |
| Cmax Range (mcg/ml) | 13.9–2.3 | 2.8–0.5 |
| AUC[3] 0–24 hrs (average) | 57.6 ± 40.2 | 12.2 ± 7.9 |
| Cmax Normalized (mcg/ml)[4] | 6.64 | 1.6 |
| AUC 0–24 hrs Normalized[4] | 46.08 | 12.2 |

[1] The capsules were coated with Opadry Enteric Orange (approximately 8% of total capsule weight excluding the capsule itself).
[2] 300 mg and 240 mg of ceftriaxone sodium are equivalent to 250 mg and 200 mg of ceftriaxone, respectively. Formulation 1 and Formulation 2 contain 250 mg and 200 mg dose of ceftriaxone, respectively. Due to the viscosity difference in the components of these formulations. Formulation 2 could accommodate only a 200 mg dose in #0 size capsule.
[3] AUC = Area under curve.
[4] Average is normalized to a 200 mg dose of ceftriaxone.

TABLE 3B (Two capsules)
ORAL ABSORPTION OF CEFTRIAXONE IN HUMANS
FORMULATIONS

| INGREDIENTS (per capsule)[1] | FORMULA 1 (mg) | FORMULA 2 (mg) |
|---|---|---|
| CEFTRIAXONE, SODIUM[2] | 300 | 240 |
| LAURETH-12 | 120 | 120 |
| SODIUM CAPRYLATE | 100 | 100 |
| MIGLYOL-812 | 250 | — |
| WITEPSOL-H15 | — | 230 |
| TOTAL | 770 | 690 |
| CEFTRIAXONE DOSE[2] | 500 | 400 |
| RESULTS | | |
| Cmax mcg/ml (average) | 9.9 ± 6.0 | 5.9 ± 6.7 |
| Cmax Range (mcg/ml) | 20.7–3.5 | 15.9–1.7 |
| AUC[3] 0–24 hrs | 68.1 ± 36.7 | 46.1 ± 49.9 |
| Cmax Normalized (mcg/ml)[4] | 7.92 | 5.9 |
| AUC 0–24 hrs Normalized[4] | 54.48 | 46.1 |

[1] The capsules were coated with Opadry ® Enteric Orange (approximately 8% of total capsule weight).
[2] 300 mg and 240 mg of ceftriaxone sodium are equivalent to 250 mg and 200 mg ceftriaxone, respectively. Formulation 1 and Formulation 2 contain 250 mg and 200 mg dose of ceftriaxone, respectively. Due to the viscosity difference in the components of these formulations. Formulation 2 could accommodate only a 200 mg dose in #0 size capsule.
[3] AUC = Area under curve.
[4] Average is normalized to a 200 mg dose of ceftriaxone.

The data shows the superiority of inventive Formula 1 (Miglyol-812) to prior art Formula 2 (Witepsol-H15), especially for Cmax Range and AUC. In particular, the AUC obtained with one capsule of inventive Formula I was over 4¼ times the AUC for one capsule of prior art Formula 2 (about 4 times when normalized). Similarily, the AUC obtained with two capsules of inventive Formula 1 was about 1¼ times the AUC for two capsules of prior art Formula 2 (about 1.2 times when normalized). Since the AUC results are superior for inventive Formula 1 over prior Formula 2, it is of no matter that a lower amount (80% by weight) of ceftriaxone sodium was used for prior art Formula 2 than inventive Formula 1. Moreover, the Cmax Range for inventive Formula 1 was superior to that of prior art Formula 2 for one and two capsule administration. Since the low range of Cmax for prior art Formula 2 is less than 2 mcg/ml, Formula 2 also would not be therapeutically effective in all patients.

Formulation Examples

By way of illustration, suitable formulations for dosage forms in accordance with this invention are set forth in Examples 4 and 5. While ceftriaxone, the preferred antibiotic for this invention, is used in these formulations, it should be understood that other antibiotics may be substituted in appropriate amounts within the knowledge of one skilled in the art.

EXAMPLE 4

Oral Dosage Form

| | mg/capsule | | |
|---|---|---|---|
| Ceftriaxone, Sodium | 300 mg | 300 mg | 300 mg |
| Laureth-12 | 120 mg | 150 mg | 200 mg |
| Sodium caprylate | 100 mg | 90 mg | 50 mg |
| Migloyl-812 | 250 mg | 230 mg | 220 mg |
| | 770 mg | 770 mg | 770 mg |

To prepare the above formulation, the vehicle Migloyl 812 is warmed to 55° C. and the absorption enhancer system components (Laureth-12 and sodium caprylate), are added with mixing. The mixture is then cooled to 45° C. and the drug (ceftriaxone sodium) is added to the mixture. The resulting solution is mixed until uniformly distributed and free of any aggregates. The mass is homogenized, if necessary, to obtain a uniform suspension. The suspension is filled into gelatin capsules, sealed if necessary, and the capsules are enteric coated.

EXAMPLE 5

Enteric Coating Formulations

| Ingredients | % w/w |
|---|---|
| Preparation A: | |
| Hydroxypropyl methylcellulose phthalate ("HPMCP") | 5.0 |
| Triacetin | 0.5 |
| Alcohol USP | 7.9 |
| Water | 15.5 |
| Preparation B: | |
| HPMCP | 10.0 |
| Titanium dioxide | 0.2 |
| Dimethyl polysiloxane | 0.05 |
| Triethyl citrate | 1.0 |
| Alcohol USP | 72.75 |
| Water | 16.00 |
| Preparation C: | |
| Cellulose acetate phthalate ("CAP") | 8.5 |
| Diethyl phthalate | 1.5 |
| Titanium dioxide | 0.2 |
| Acetone | 44.9 |
| Denatured alcohol | 44.9 |
| Preparation D: | |
| Polyvinyl acetate phthalate ("PVAP") | 5.0 |
| Acetylated glycerides | 0.8 |
| Methylene chloride | 47.1 |
| Denatured alcohol | 47.1 |
| Preparation E: | |
| Methacrylic acid or methacrylic acid ester (Eudragit ® S or L, manufactured by Rohm Pharma, GMBH, Wetterstadt, West Germany) | 8.0 |
| Acetone | 46.0 |
| Anhydrous alcohol | 46.0 |
| Plasticizer | q.s. |

The enteric polymer with plasticizers is dissolved in solvents described under each formulation to form a suspension/solution. An opacifer such as titanium dioxide is added, if necessary. The enteric coating of the capsules is performed by spraying the coating suspension/solution on the capsules in a suitable coating vessel. Approximately 7-8% by weight of the enteric polymer coating is used for adequate enteric properties.

We claim:

1. A method for treating a bacterial infection in a human comprising orally administering to the human a therapeutic effective amount of a pharmaceutical suspension composition comprising:

a) a water-soluble cephalosporin;
b) an absorption enhancing amount of an absorption enhancing system including:

$$CH_3(CH_2)_{10}CH_2(OCH_2CH_2)_nOH \quad (1)$$

wherein n has an average value of 12; and 2) a pharmaceutically acceptable salt of at least one of caprylic or capric acid wherein the ratio of component (b)(1) to component (b)(2) is from about 1:6 to about 6:1; and c) a compound of the formula:

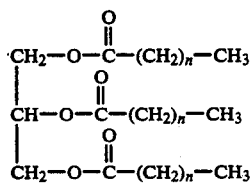

$$\begin{array}{c} O \\ \parallel \\ CH_2-O-C-(CH_2)_n-CH_3 \\ | \quad O \\ \quad \parallel \\ CH-O-C-(CH_2)_n-CH_3 \\ | \quad O \\ \quad \parallel \\ CH_2-O-C-(CH_2)_n-CH_3 \end{array}$$

wherein n is 6 or 8, said suspension composition having been placed in a capsule which is coated with a pharmaceutically acceptable enteric coating.

2. The method according to claim 1, in which component (b)(2) is an alkali metal or alkaline earth metal salt of caprylic or capric acid.

3. The method of claim 1, wherein component (b)(2) is sodium caprylate, potassium caprylate or calcium caprylate.

4. The method of claim 3, wherein component (b)(2) is sodium caprylate.

5. The method according to claim 1, in which the cephalosporin is ceftriaxone or a pharmaceutically acceptable salt, ester or hydrate thereof.

6. The method according to claim 4, in which the cephalosporin is ceftriaxone or a pharmaceutically acceptable salt, ester or hydrate thereof.

7. The method according to claim 6, wherein the enteric coating is polyvinyl acetate phthalate.

8. A unit dose pharmaceutical composition comprising:

a) a therapeutically effective amount of water soluble cephalosporin;
b) an absorption enhancing amount of an absorption enhancing system including:

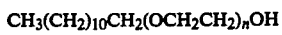

$$CH_3(CH_2)_{10}CH_2(OCH_2CH_2)_nOH \quad (1)$$

wherein n has an average value of 12; and 2) a pharmaceutically acceptable salt of at least one of caprylic or capric acid, wherein the ratio of component (b)(1) to component (b)(2) is from about 1:6 to about 6:1; and c) a compound of the formula:

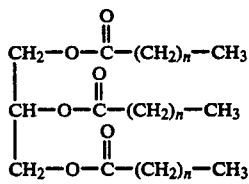

$$\begin{array}{c} O \\ \parallel \\ CH_2-O-C-(CH_2)_n-CH_3 \\ | \quad O \\ \quad \parallel \\ CH-O-C-(CH_2)_n-CH_3 \\ | \quad O \\ \quad \parallel \\ CH_2-O-C-(CH_2)_n-CH_3 \end{array}$$

wherein n is 6 or 8, said suspension composition having been placed in a capsule that is coated with a pharmaceutically acceptable enteric coating.

9. The pharmaceutical composition according to claim 8, in which component (b)(2) is an alkali metal or alkaline earth metal salt of caprylic acid.

10. The pharmaceutical composition of claim 8, wherein component (b)(2) is sodium caprylate, potassium caprylate or calcium caprylate.

11. The pharmaceutical composition of claim 8, wherein component (b)(2) is sodium caprylate.

12. The pharmaceutical composition according to claim 8, in which the cephalosporin is ceftriaxone or a pharmaceutically acceptable salt, ester or hydrate thereof.

13. The pharmaceutical composition according to claim 11, in which the cephalosporin is ceftriaxone or a pharmaceutically acceptable salt, ester or hydrate thereof.

14. The pharmaceutical composition of claim 13, wherein the ratio of component (b)(1) to (b)(2) is about 1 to about 1.

15. The pharmaceutical composition of claim 13, wherein the ratio of component (b)(1) to (b)(2) is about 6 to about 5.

16. The pharmaceutical composition of claim 8, wherein the cephalosporin is ceftriaxone or a pharmaceutically acceptable salt, ester or hydrate thereof; component (b)(2) is sodium caprylate; the weight ratio of component (b)(1) to component (b)(2) is about 1:6 to about 6:1; and the enteric coating material is polyvinyl acetate phthalate.

* * * * *